US011767539B2

(12) United States Patent
Xie et al.

(10) Patent No.: US 11,767,539 B2
(45) Date of Patent: Sep. 26, 2023

(54) VIRAL VECTOR PRODUCTION

(71) Applicant: University of Massachusetts, Boston, MA (US)

(72) Inventors: Jun Xie, Shrewsbury, MA (US); Guangping Gao, Westborough, MA (US)

(73) Assignee: University of Massachusetts, Boston, MA (US)

( * ) Notice: Subject to any disclaimer, the term of this patent is extended or adjusted under 35 U.S.C. 154(b) by 892 days.

(21) Appl. No.: 16/612,497

(22) PCT Filed: May 11, 2018

(86) PCT No.: PCT/US2018/032291
§ 371 (c)(1),
(2) Date: Nov. 11, 2019

(87) PCT Pub. No.: WO2018/209216
PCT Pub. Date: Nov. 15, 2018

(65) Prior Publication Data
US 2020/0199622 A1    Jun. 25, 2020

Related U.S. Application Data

(60) Provisional application No. 62/505,540, filed on May 12, 2017.

(51) Int. Cl.
C12N 15/86        (2006.01)
C12N 15/113       (2010.01)
C12Q 1/68         (2018.01)

(52) U.S. Cl.
CPC ............ *C12N 15/86* (2013.01); *C12N 15/113* (2013.01); *C12N 2310/141* (2013.01); *C12N 2740/15043* (2013.01); *C12N 2740/15052* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

2003/0138772 A1    7/2003  Gao et al.
2016/0333373 A1*  11/2016  Farley ................... C12N 15/86

FOREIGN PATENT DOCUMENTS

WO    WO 2007/000668 A2    1/2007
WO    WO 2017/189901 A1    11/2017

OTHER PUBLICATIONS

Maunder et al., Nature Communications 8:14834, pp. 1-13, Mar. 27, 2017.*

Partial Supplementary European Search Report for Application No. EP 18797830.9, dated Jan. 13, 2021.
Extended European Search Report for Application No. EP 18797830.9, dated Apr. 19, 2021.
Reid et al., Micro-RNA induced silencing of cytotoxic transgenes leads to increased recombinant adeno-associated virus (AAV) titers. ARVO Annual Meeting Abstract. Sep. 2016.
Wang et al., An shRNA silencing a non-toxic transgene reduces nutrient consumption and increases production of adenoviral vectors in a novel packaging cell. J Cell Physiol. May 2009;219(2):365-71. doi: 10.1002/jcp.21679.
Xie et al., RNA Interference Mediated Ablation of Cytotoxic Transgenes Enables Productive Viral Vector Packaging. Abstract 772. Molecular Therapy. May 2017; 25(5S1):357-358.
International Search Report and Written Opinion for Application No. PCT/US2018/032291, dated Jul. 19, 2018.
International Preliminary Report on Patentability for Application No. PCT/US2018/032291, dated Nov. 21, 2019.
Mccarty, Self-complementary AAV vectors; advances and applications. Mol Ther. Oct. 2008;16(10):1648-56. doi: 10.1038/mt.2008.171. Epub Aug. 5, 2008.
Mtetzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi: 10.1089/hum.2015.050. Epub Aug. 6, 2015.
Palmer et al., Helper virus-mediated downregulation of transgene expression permits production of recalcitrant helper-dependent adenoviral vector. Mol Ther Methods Clin Dev. Jun. 8, 2016;3:16039. doi: 10.1038/mtm.2016.39. eCollection 2016.
Tai et al., Adeno-associated Virus Genome Population Sequencing Achieves Full Vector Genome Resolution and Reveals Human-Vector Chimeras. Mol Ther Methods Clin Dev. Feb. 13, 2018;9:130-141. doi: 10.1016/j.omtm.2018.02.002. eCollection Jun. 15, 2018.
Xie et al., 555. AAV Vector-Mediated Efficient and Sustained miRNA Antagonism In Vivo for Studying miRNA Function and Treating Hyperlipidemia. Mol Ther. May 1, 2011;19(Suppl 1):S213. doi: https://doi.org/10.1016/S1525-0016(16)37128-3. 1 page.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., RNA interference-mediated ablation of cytotoxic transgenes enables productive viral vector packaging. Presented at ASGCT 20th Annual Meeting on May 13, 2017. Abstract. 1 page.
Xie et al., RNA interference-mediated ablation of cytotoxic transgenes enables productive viral vector packaging. Presented at ASGCT 20th Annual Meeting on May 13, 2017. Slideshow Presentation. 22 pages.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
PCT/US2018/032291, Jul. 19, 2018, International Search Report and Written Opinion.
PCT/US2018/032291, Nov. 21, 2019, International Preliminary Report on Patentability.

* cited by examiner

*Primary Examiner* — Sean McGarry
(74) *Attorney, Agent, or Firm* — Wolf, Greenfield & Sacks, P.C.

(57) ABSTRACT

In some aspects, the disclosure relates to methods for improving titer and yield of viral vector production. In some embodiments, the methods comprise transient silencing of transgene expression during packaging of a viral vector.

11 Claims, 8 Drawing Sheets
Specification includes a Sequence Listing.

VIRAL VECTOR PRODUCTION

RELATED APPLICATIONS

This Application is a national stage filing under 35 U.S.C. § 371 of international PCT application PCT/US2018/032291, filed May 11, 2018, entitled "VIRAL VECTOR PRODUCTION," which claims the benefit under 35 U.S.C. § 119(e) of the filing date of U.S. Provisional Application Ser. No. 62/505,540, filed May 12, 2017, the entire contents of each of which are incorporated herein by reference.

BACKGROUND

Viral vector-mediated gene transfer is a valuable tool for studying gene functions and gene therapeutics. However, production of viral vectors comprising certain transgenes (e.g., transgene products that are toxic to packaging cells or incompatible with viral vector packaging systems) faces several challenges, for example, very low titer or no production of viral vectors.

SUMMARY

In some aspects, the disclosure relates to abolishing transgene expression by RNA degradation (e.g., as mediated by short-hairpin RNAs (shRNAs), artificial miRNAs (amiRNAs), etc.) during the vector packaging process to allow for efficient production of vectors (e.g., viral vectors) comprising transgene products that are cytotoxic and/or incompatible with a viral vector packaging system.

Accordingly in some aspects, the disclosure provides a method for controlling or improving recombinant virus production yield comprising: introducing into a host cell a first nucleic acid comprising a transgene; introducing into the host cell a second nucleic acid capable of expressing an interfering nucleic acid, wherein the interfering nucleic acid specifically inhibits expression of the transgene; replicating the nucleic acid comprising the transgene within the host cell; and, optionally, isolating a virus particle comprising the first nucleic acid from the host cell.

In some embodiments, the first nucleic acid and the second nucleic acid are introduced into the host cell simultaneously. In some embodiments, the first nucleic acid and the second nucleic acid are introduced into the host cell separately. It should be appreciated that, in some embodiments, the first nucleic acid and the second nucleic acid are located on the same plasmid. In some embodiments, the inhibition of transgene expression by the second nucleic acid is transient. In some embodiments, the inhibition of transgene expression by the second nucleic acid is permanent.

In some embodiments, a host cell is a viral vector packaging cell. In some embodiments, the host cell is a mammalian cell. In some embodiments, a mammalian cell is a human cell, for example a HEK293T cell. In some embodiments, a host cell is an insect cell. In some embodiments, a host cells is an insect cell, for example a *Spodoptera frugiperda* (Sf9) cell.

In some embodiments, a first nucleic acid is a lentiviral transfer plasmid, an adeno-associated virus (AAV) vector, an adenovirus (Ad) vector, or a retroviral vector. In some embodiments, a first nucleic acid is a lentiviral transfer plasmid and comprises at least one long terminal repeat (LTR). In some embodiments, a first nucleic acid is an AAV vector and comprises at least one inverted terminal repeat (ITR). In some embodiments, a first nucleic acid is a retroviral transfer plasmid and comprises at least one long terminal repeat (LTR).

In some embodiments, an AAV ITR is an AAV1, AAV2, AAV3, AAV4, AAV5, AAV6, AAV7, AAV8, or AAV9 ITR. In some embodiments, an AAV vector is a self-complementary AAV (scAAV) vector comprising at least one ΔITR or mutant ITR (mTR).

In some embodiments, expression of a transgene interferes with viral vector packaging (e.g., via a product of the transgene) in a host cell. In some embodiments, the transgene is cytotoxic or forms a secondary structure with high thermal stabilities (e.g., has one or more physiochemical properties that are detrimental to the fitness of the host cell).

In some embodiments, a transcript encoded by the first nucleic acid comprises one or more binding sites for an inhibitory nucleic acid. In some embodiments, one or more binding sites are located between the last codon and the polyA tail of the transcript. In some embodiments, one or more binding sites are located in a 5' untranslated region (5'UTR) of the transcript. In some embodiments, one or more binding sites are located between the last codon and the polyA tail of the transcript and one or more binding sites are located in a 5'UTR of the transcript. In some embodiments the one or more binding sites comprise a miR-333 binding site (SEQ ID NO: 3), a miR-865 binding site (SEQ ID NO: 4), or a combination thereof. In some embodiments, the one or more binding sites are 1, 2, or 3 binding sites.

In some embodiments, an inhibitory nucleic acid is a micro-RNA (miRNA) or an artificial miRNA (amiRNA). In some embodiments, the sequence of an inhibitory nucleic acid binding site is not recognized by endogenous miRNAs of a host cell.

In some embodiments, a second nucleic acid expresses a short hairpin RNA, miRNA, or an amiRNA. In some embodiments, the second nucleic acid expresses a miRNA or an amiRNA. In some embodiments, a miRNA or amiRNA comprises a miRNA sequence expressed in a non-human cell (e.g., a miRNA sequence that is naturally expressed only in non-human cells). In some embodiments, a miRNA or amiRNA comprises a miRNA sequence expressed in an insect cell or a plant cell (e.g., a miRNA sequence that is naturally expressed only in an insect cell or a plant cell). In some embodiments, a miRNA or amiRNA comprises a miRNA sequence expressed in a plant cell (e.g., a miRNA sequence that is naturally expressed only in a plant cell). In some embodiments, an miRNA or amiRNA comprises a miR-333 sequence (SEQ ID NO: 1) or a miR-856 sequence (SEQ ID NO: 2). In some embodiments, an amiRNA comprises a miR-30 scaffold (e.g., backbone sequence, such as a pri-miR30a backbone sequence). In some embodiments, a transcript comprises one or more binding sites for a miR-333 sequence or a miR-856 sequence.

In some embodiments, a host cell further comprises one or more accessory plasmids. In some embodiments, one or more accessory plasmids are a packaging plasmid, an Env encoding plasmid, a Rev encoding plasmid, a Rep encoding plasmid, or a Cap encoding plasmid.

In some embodiments, a transgene expressed from the virus particle isolated from the host cell is functional.

1 are useful for delivery of one or more transgenes to a subject (e.g., a cell of a subject).

Figure 2A:
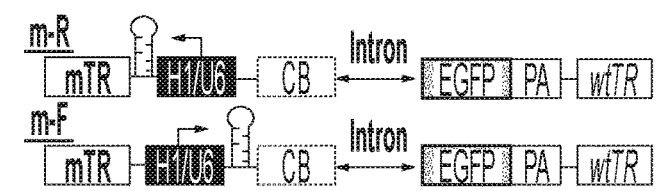
Figure 2A:
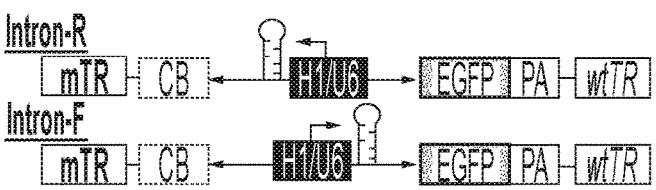
Figure 2A:
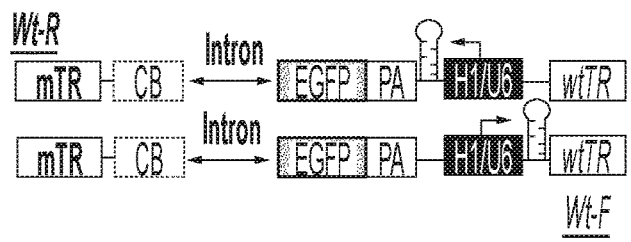
Figure 2B:
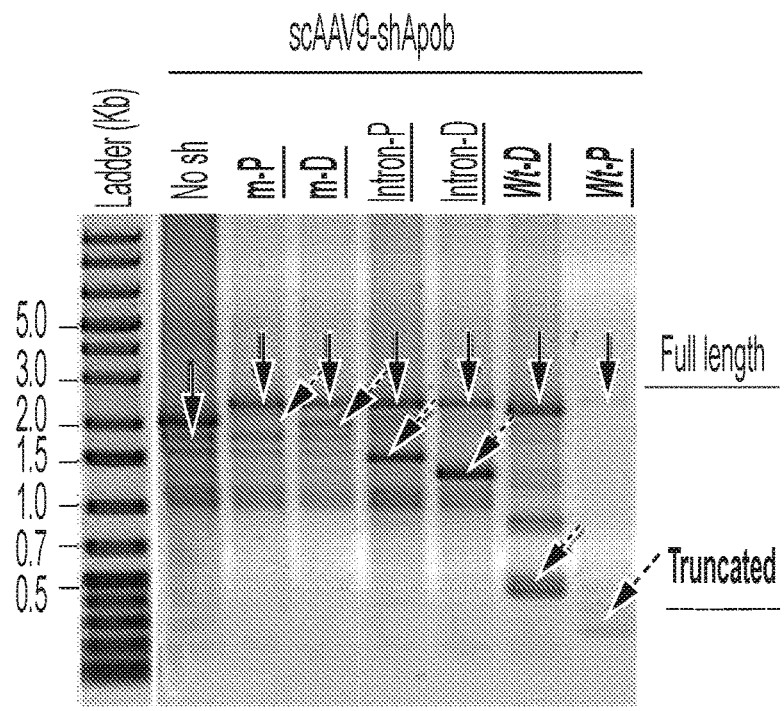
Figure 2C:
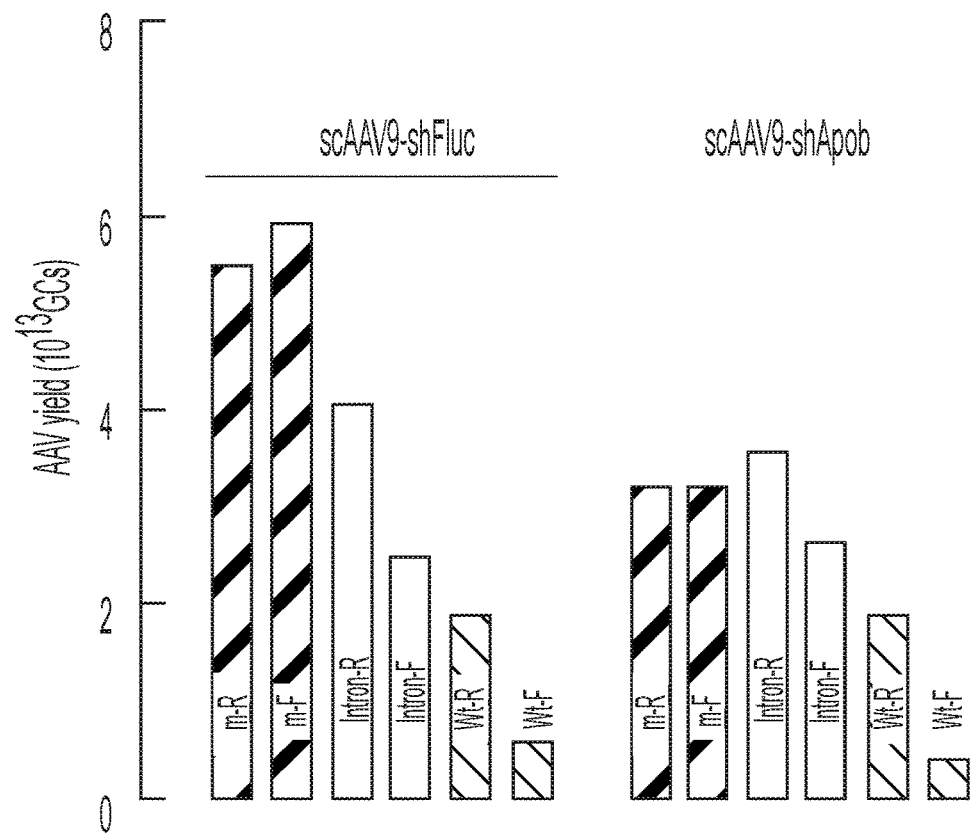

FIGS. 2A-2C show palindrome sequences compromise rAAV genome homogeneity and yield. FIG. 2A shows a schematic of self-complementary AAV (scAAV) plasmids comprising a CMV enhancer/chicken (β-actin promoter (CB), an EGFP reporter gene, and a beta-globin polyA sequence (PA). shRNA cassettes targeting Apob, driven by the H1 promoter, or targeting the Firefly luciferase gene (Fluc), driven by the U6 promoter, were inserted adjacent to the mTR (m-R and m-F), within the intron (Intron-R and Intron-F), or adjacent to the wtTR (Wt-R and Wt-F). FIG. 2B shows agarose gel analysis of self-complementary AAV vector genomes carrying shApob, driven by the H1 promoter, or shFluc (not shown), driven by the U6 promoter. Cassettes were each tested in the six positions/orientations as illustrated in the left side of the figure. Truncated viral genomes were observed in lanes for all shRNA cassettes but not in control cassette (no shRNA). FIG. 2C shows vectors depicted in (FIG. 2A) were packaged into AAV9 capsids and assessed for yield by qPCR using an EGFP primer/probe set. Constructs carrying the same shRNA cassette were packaged and titrated as a set (at the same time) to ensure fair comparisons. The two sets of constructs (U6-shFluc and H1-shApob) were packaged at different times.

Figure 3:
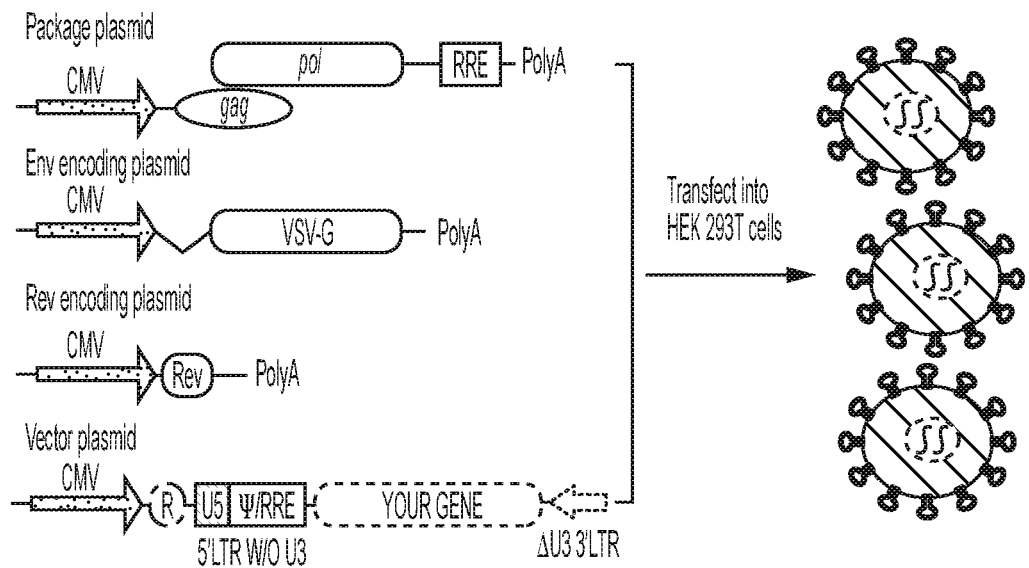

FIG. 3 shows a schematic depiction of $3^{rd}$ generation lentiviral vector production. In this embodiment, four constructs (packaging plasmid, Rev encoding plasmid, Env encoding plasmid, transgene encoding plasmid) are transfected into a permissive cell line (e.g., HEK293) to produce the vectors.

Figure 4:
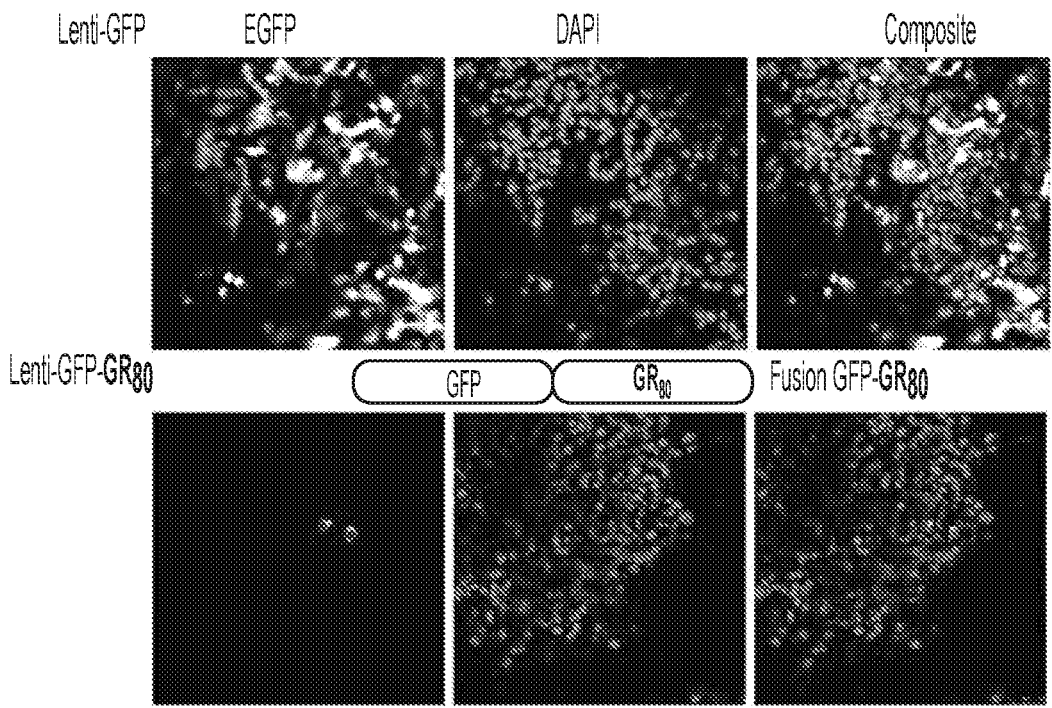

FIG. 4 shows cells infected with a lentiviral vector expressing either GFP (Lenti-GFP, top) or GFP fused to an 80-mer Glycine-Arginine (Lenti-GFP-GR$_{80}$) di-amino acid repeat peptide. GR$_{80}$ is a cytotoxic amyotrophic lateral sclerosis (ALS) and frontotemporal dementia (FTD)-related peptide. Fluorescence imaging shows lower transduction of cells by Lenti-GFP-GR$_{80}$ compared to Lenti-GFP, indicating lower replication or packaging efficiency of the vector comprising cytotoxic protein (GR$_{80}$) relative to vector comprising GFP.

Figure 5:
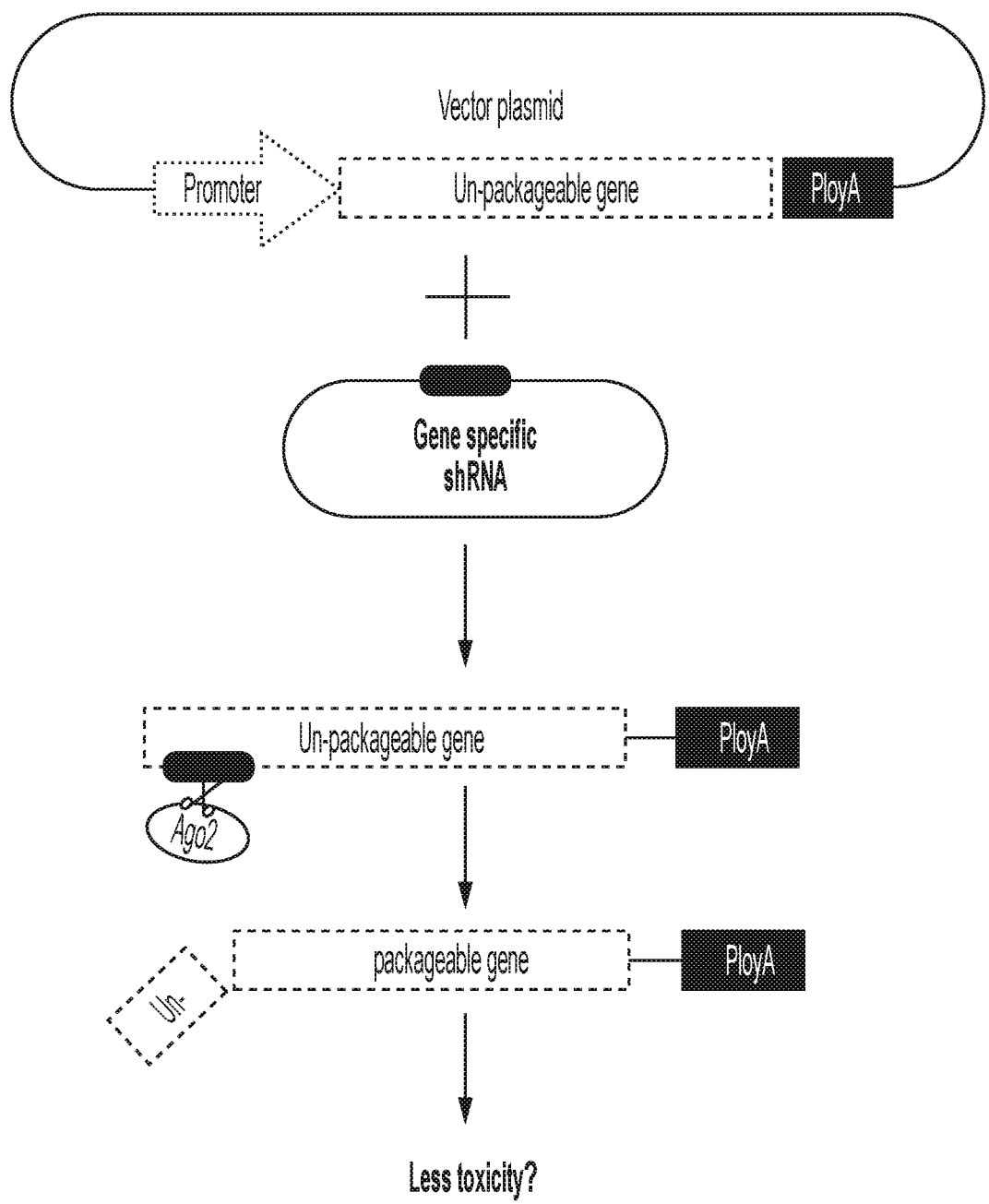

FIG. 5 shows a schematic depiction of a strategy for increasing replication and/or packaging of a viral vector comprising transgene resistant to packaging (e.g., a cytotoxic transgene or a transgene that reduces fitness of a host cell). Packaging cells are co-transfected with the viral vector production plasmid(s) and a plasmid capable of expressing an interfering RNA molecule (e.g., shRNA, dsRNA, etc.) specific for the transgene resistant to packaging (e.g., a cytotoxic transgene or a transgene that reduces fitness of a host cell). Transient silencing of transgene expression during packaging (e.g., mediated by RNAi machinery such as Ago2) increases viral vector replication and packaging, leading to an increased yield.

Figure 6:
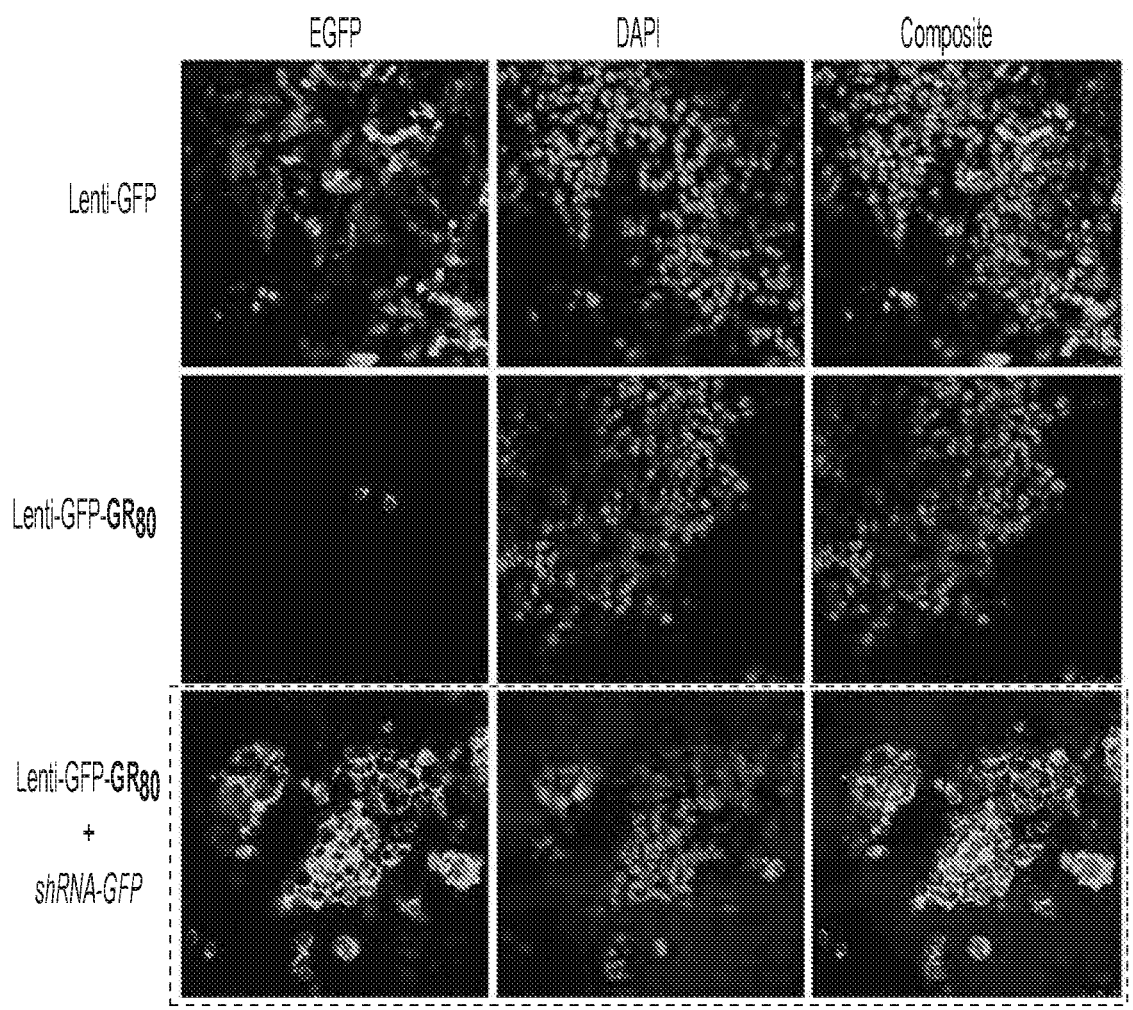

FIG. 6 shows cells infected with a lentiviral vector expressing either GFP (Lenti-GFP, top), Lenti-GFP-GR$_{80}$, or Lenti-GFP-GR$_{80}$ that was packaged during transient gene expression silencing by a plasmid expressing Lenti-GFP-GR$_{80}$-specific shRNA (shRNA-GFP). Fluorescence imaging shows lower transduction of cells by Lenti-GFP-GR$_{80}$ compared to Lenti-GFP, indicating lower replication or packaging efficiency of the vector comprising cytotoxic protein (GR$_{80}$) relative to vector comprising GFP. However, significantly increased infection and expression of GFP-GR$_{80}$ was observed in cells transduced with Lenti-GFP-GR$_{80}$, indicating that transient silencing of transgene expression during vector packaging results in high titer and functional viral vectors.

Figure 7:
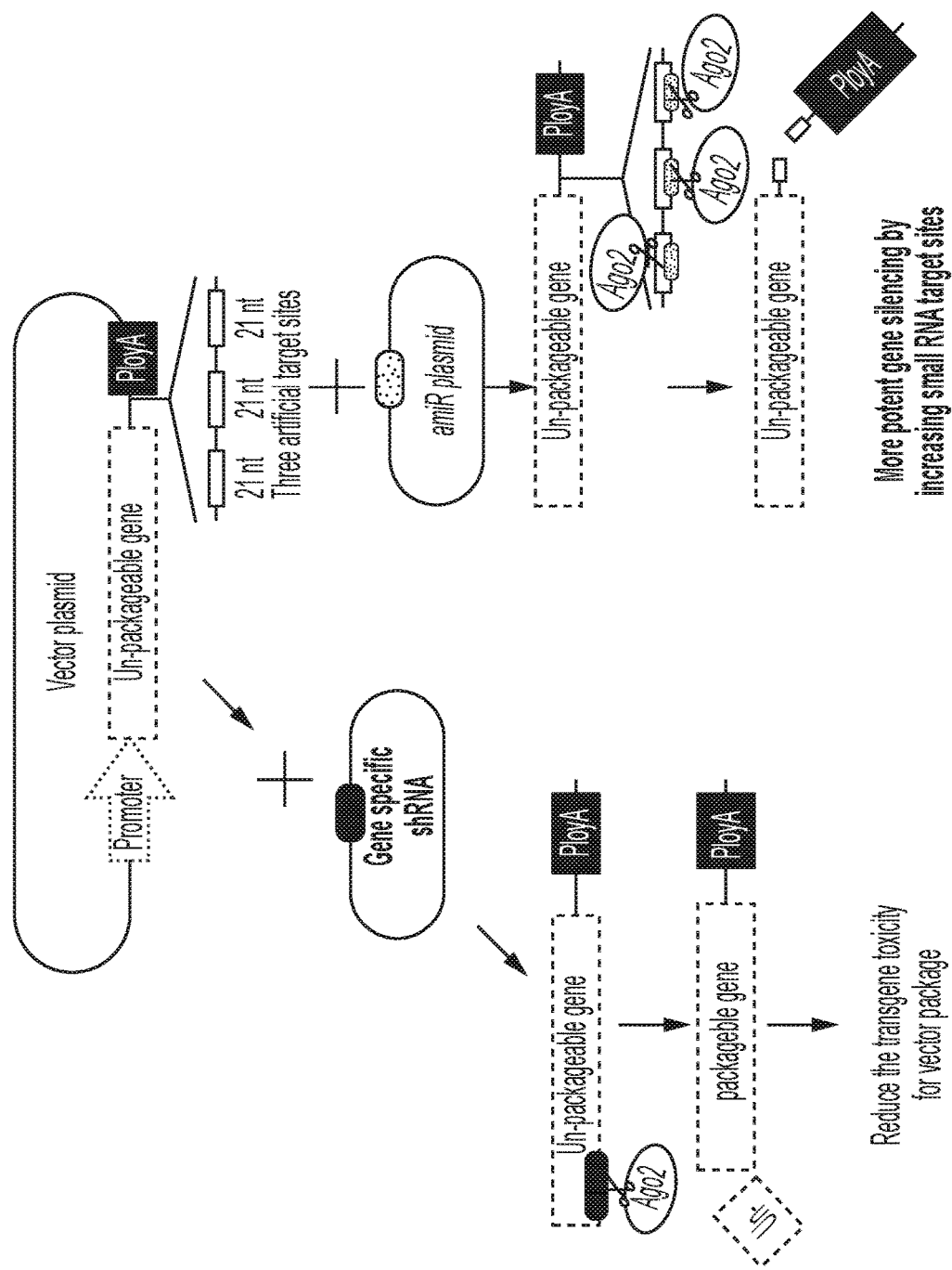

FIG. 7 shows a schematic depiction of two strategies for increasing replication and/or packaging of a viral vector comprising a transgene resistant to packaging (e.g., a cytotoxic transgene or a transgene that reduces fitness of a host cell). On the left, packaging cells are co-transfected with the viral vector production plasmid(s) and a plasmid capable of expressing an shRNA specific for the transgene. Transient silencing of transgene expression during packaging (e.g., mediated by RNAi machinery such as Ago2) increases viral vector replication and packaging, leading to an increased yield. On the right, one or more (e.g., 3) artificial miRNA (amiRNA) binding sites are engineered into the plasmid comprising transgene resistant to packaging (e.g., a cytotoxic transgene or a transgene that reduces fitness of a host cell). Packaging cells are co-transfected with the viral vector production plasmid(s) and a plasmid capable of expressing an amiRNA that is specific for the binding sites engineered into the production plasmid.

Figure 8:
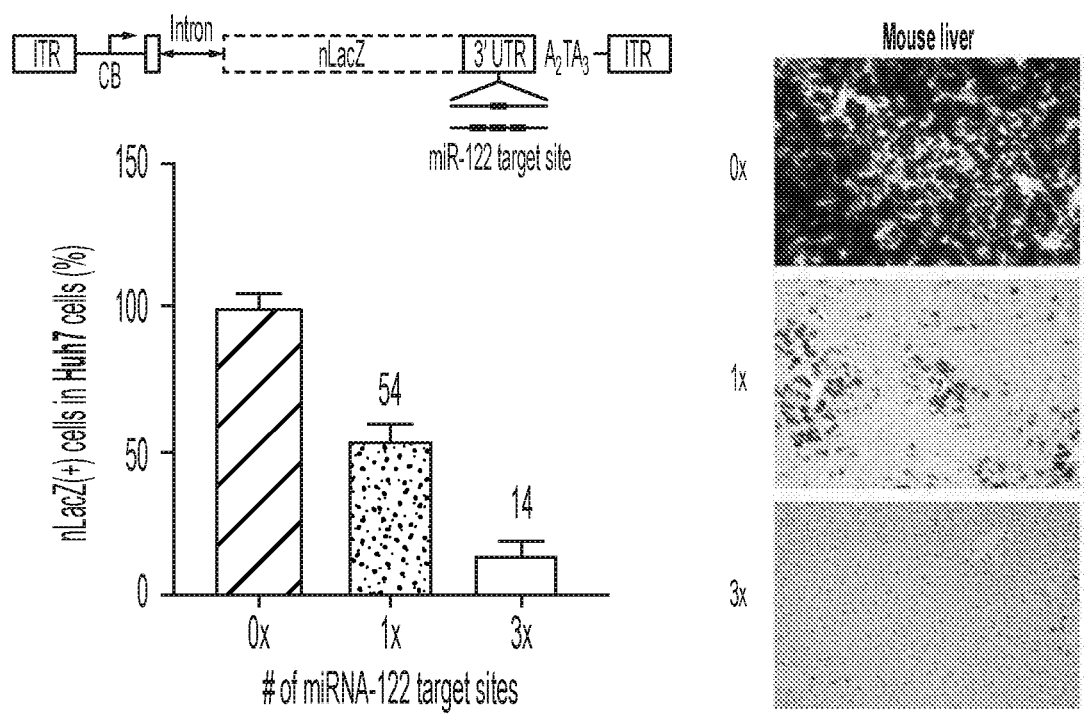

FIG. 8 shows exemplary data demonstrating that RNAi potency increases when an increasing number of miRNA binding sites is incorporated into a transgene construct. In this example, zero, one, or three miR-122 binding sites were incorporated into a nLacZ expression construct. Huh7 cells were transfected with each construct and nLacZ expression was measured. Data indicate decreased transgene (nLacZ) expression in cells transfected with constructs having one or three miR-122 binding sites. A similar decrease in transgene expression was also observed in mouse livers.

Figure 9:
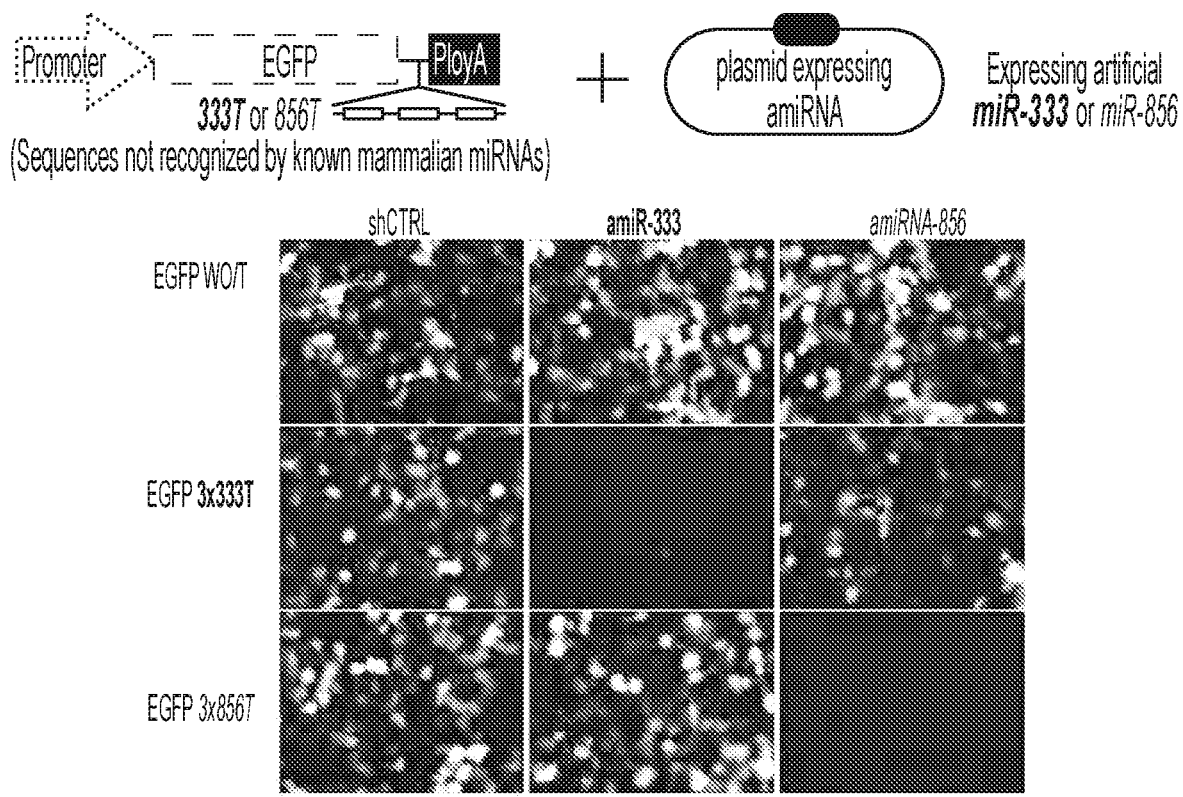

FIG. 9 shows specific and efficient gene silencing by the interaction between artificial miRNA (amiRNA) and their target sites. Cells were co-transfected with an EGFP construct comprising multiple miRNA binding sites, specific for either 333T or 856T (which are sequences that are not bound by known mammalian miRNAs), and a plasmid expressing either miR-333 or miR-856 amiRNA. Data indicate silencing of EGFP-333T expression in cells that were co-transfected with miR-333 amiRNA but not miR-856 amiRNA or a shRNA control plasmid. Data indicate silencing of EGFP-856T expression in cells that were co-transfected with miR-856 amiRNA but not miR-333 amiRNA or a shRNA control plasmid.

Figure 10:
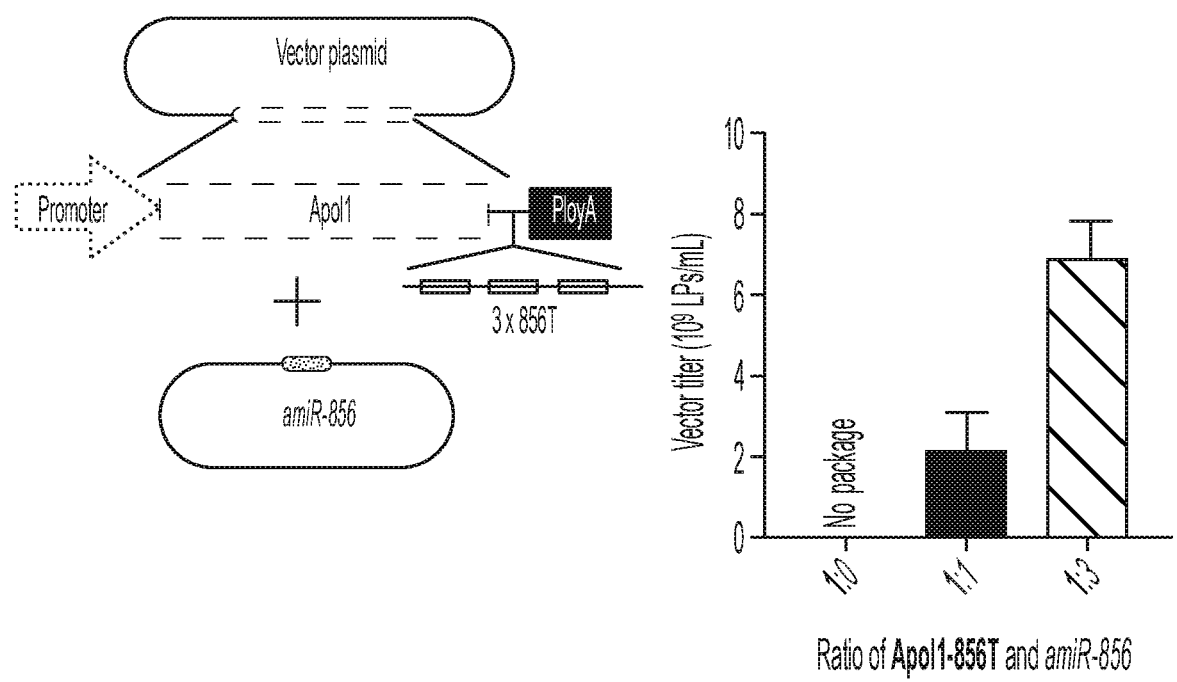

FIG. 10 shows representative data relating to methods for improving titer and vector packaging for a lentiviral vector capable of expressing apolipoprotein L1 (Apol1), which typically is difficult to package using conventional viral vector production procedures. Three miR-856 binding sites (3×856T) were incorporated into a Apol1 expression construct. Packaging cells were co-transfected with the Apol1 expression construct and a plasmid expressing amiR-856. Data show that vector titer increases with an increasing amiR-856 concentration, indicating that increased silencing of transgene (e.g., Apol1) expression during packaging increases efficiency of Lenti-Apol1 vector production.

Figure 11:
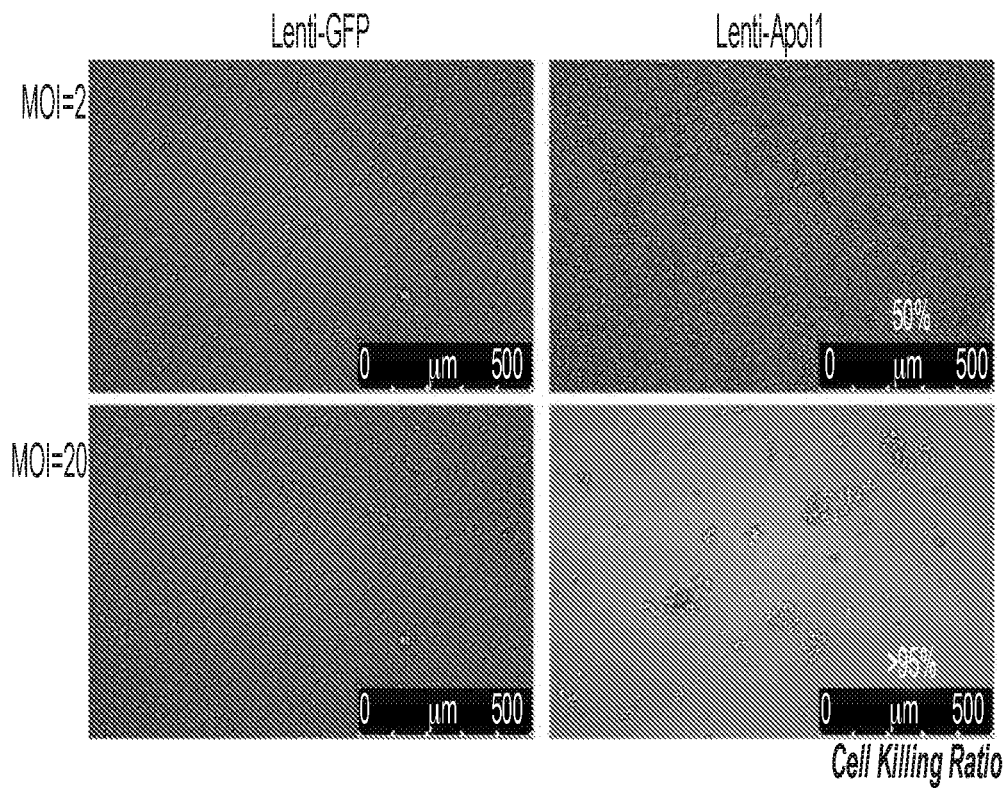

FIG. 11 shows representative data indicating that apolipoprotein L1 expressed by vector (e.g., Lenti-Apol1) that has been packaged during silencing of transgene expression is functional, as indicated by death of cells infected with Lenti-Apol1 vector but not control Lenti-GFP vector.

DETAILED DESCRIPTION

Aspects of the disclosure relate, in part, to the discovery that abolishing transgene expression by RNA interference or similar pathway (either shRNAs or artificial miRNAs, amiRNAs) during vector packaging (e.g., packaging of recombinant viral particles in host cell) results in efficient vector production. As described in the Examples below, lentiviral vectors carrying cytotoxic transgenes (e.g., EGFP-(GR)80 or ApoL1) were produced by performing co-transfection of plasmid expressing transgene-specific inhibitory nucleic acids (e.g., shRNA or miRNA) during viral vector packaging. The efficient production of viral particles comprising these exemplary genes using methods described herein is surprising because generally cytotoxic genes are difficult to package by using conventional viral particle production methods.

A second strategy for viral vector production is also described herein. Briefly, three copies of target sites for either shRNAs or artificial miRNAs were incorporated into the 3'UTR of ApoL1 transgene in the Lenti-ApoL1 plasmid. Those target sites were designed not to be recognized by any known mammalian endogenous small RNAs (e.g., the miRNA binding sites are orthogonal with respect to a host cell) but specifically sensitive to the shRNA or amiRNA (e.g., orthogonal shRNA or amiRNA) expressed from a co-transfected plasmid in the packaging process. An "orthogonal" inhibitory nucleic acid or nucleic acid binding site refers to a sequence of an inhibitory nucleic acid (or it's cognate binding site) that is not naturally expressed in a host cell and does not interact with miRNAs (or miRNA binding sites) endogenously expressed by a host cell. It was observed that production of viral vectors having transgene embedded with the artificial small RNA target sites is not compromised. Instead, transgene expression is efficiently silenced in the presence of the corresponding shRNA or amiRNA (e.g., transiently silenced during viral particle packaging). Accordingly, virus particles comprising a cytotoxic transgene were successfully produced with a high titer. Additionally, it was observed that infection of HEK293 cells with the viral particles caused massive cell death, indicating the infectivity of packaged viral vector and maintenance of transgene function.

In summary, suppression of the cytotoxic or incompatible transgenes during vector production by transient RNA silencing enables the production of high titer and functional viral vectors. Methods described by the disclosure, in some embodiments, are useful for the packaging of viral vectors such as Adenovirus, lentivirus vectors, adeno-associated virus (AAV), etc., carrying cytotoxic or incompatible transgenes (e.g., transgenes that are detrimental to the fitness of a host cell).

Nucleic Acids

As used herein, the term "nucleic acid" refers to polymers of linked nucleotides, such as DNA, RNA, etc. In some embodiments, proteins and nucleic acids of the disclosure are isolated. In some embodiments, the DNA of a transgene is transcribed into a messenger RNA (mRNA) transcript. As used herein, the term "isolated" means artificially produced (e.g., an artificially produced nucleic acid, or an artificially produced protein, such as a capsid protein). As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been artificially produced (e.g., by chemical synthesis, by recombinant DNA technology, etc.)

As used herein, a "transgene" is a nucleic acid sequence, which is not homologous to vector sequences, which encodes a polypeptide, protein, functional RNA molecule (e.g., miRNA, miRNA inhibitor) or other gene product, of interest. In some embodiments, a transgene encodes a therapeutic protein or therapeutic functional RNA. Examples of therapeutic proteins include toxins, enzymes (e.g., kinases, phosphorylases, proteases, acetylases, deacetylases, methylases, demethylases, etc.) growth factors, interleukins, interferons, anti-apoptosis factors, cytokines, anti-diabetic factors, anti-apoptosis agents, coagulation factors, anti-tumor factors, and anti-proliferative proteins. The nucleic acid coding sequence is operatively linked to regulatory components in a manner which permits transgene transcription, translation, and/or expression in a cell of a target tissue.

In some aspects, the disclosure relates to viral vectors encoding one or more transgenes that are cytotoxic or detrimental to the fitness of a host cell. A "cytotoxic" transgene refers to a transgene that encodes a gene product (e.g., a protein) that is toxic to a living cell. Examples of toxic transgenes include transgenes encoding diphtheria toxin, botulinum toxin, ribosome inactivating proteins (e.g., ricin), cytolysins, porins (e.g., actinoporins), apolipoproteins, certain proteases, etc. In some embodiments, a protein becomes cytotoxic when overexpressed in a cell. A "transgene that is detrimental to the health of a host cell" refers to a transgene encoding a protein having certain physiochemical characteristics (e.g., a secondary structure having a high thermostability, a tendency to aggregate, etc.) that results in a reduced fitness (ability to survive) of a host cell expressing that transgene relative to a host cell that does not express the transgene.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product (e.g., a therapeutic protein or therapeutic minigene) or inhibitory RNA (e.g., shRNA, miRNA, amiRNA, miRNA inhibitor) from a transcribed gene.

The term "interfering nucleic acid" as used herein, refers to a polymer of linked oligonucleotides which binds and specifically inhibit the expression of a transgene. Interfering nucleic acids can be, for example, short-interfering RNAs (siRNAs), short hairpin RNAs (shRNAs), microRNAs (miRNAs), or artificial microRNAs (amiRNA).

Short Hairpin RNAs (shRNAs)

Short hairpin RNAs (shRNAs) are artificial RNA molecules with a tight, hairpin turn. Generally, shRNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue.

Hairpin-forming RNA are useful for translational repression and/or gene silencing via the RNAi pathway. Due to having a common secondary structure, hairpin-forming RNA share the characteristic of being processed by the proteins Drosha and Dicer prior to being loaded into the RNA-induced silencing complex (RISC). Duplex length amongst hairpin-forming RNA can vary. In some embodiments, a duplex is between about 19 nucleotides and about 200 nucleotides in length. In some embodiments, a duplex is between about between about 14 nucleotides to about 35 nucleotides in length. In some embodiments, a duplex is between about 19 and 150 nucleotides in length. In some embodiments, hairpin-forming RNA has a duplex region that is 19, 20, 21, 22, 23, 24, 25, 26, 27, 28, 29, 30, 31, 32, or 33 nucleotides in length. In some embodiments, a duplex is between about 19 nucleotides and 33 nucleotides in length. In some embodiments, a duplex is between about 40 nucleotides and 100 nucleotides in length. In some embodiments, a duplex is between about 60 and about 80 nucleotides in length.

Methods of the current disclosure describe a nucleic acid expressing an interfering nucleic acid, wherein the interfering nucleic acid specifically inhibits expression of a transgene. In some embodiments, the nucleic acid expresses a shRNA, which will bind and block transcription of the transgene.

MicroRNAs (miRNAs) and Artificial microRNAs amiRNA)

MicroRNAs (miRNAs) are small, non-coding RNAs which regulate cellular gene expression by post-transcriptional silencing. When miRNAs are partially complementary to the target mRNA sequences, they typically reduce target mRNA stability and inhibit translation. In contrast, when miRNAs are nearly perfectly complementary to mRNA targets, the mRNA is cleaved, triggering its wholesale destruction. miRNA can achieve tissue specific regulation of systemically delivered and ubiquitously expressed transgenes at post-transcriptional level. miRNAs have distinct expression profiles in different tissues and cell types, which differentially regulate transcriptional profiles of cellular genes and cellular functions. Therefore, methods provided herein employ miRNAs to silence transgene expression in cells.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, a small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

Artificial microRNAs (amiRNAs) exploit the miRNA biogenesis pathway described above to produce artificially-designed small RNAs utilizing a miRNA gene backbone. The cellular processing of amiRNAs generates a single type of small RNA population which all possess the same selective nucleic acid sequence, which is generally 21 base pairs in length. AmiRNAs thereby provide a feasible method for silencing an individual transgene or simultaneously silencing closely-related gene isoforms. AmiRNAs are sometimes advantageous over traditional miRNAs because of higher gene silencing specificity and less off-target silencing effects.

In some embodiments, an artificial microRNA (amiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest (e.g., an miRNA that is orthogonal to a host cell, for example miR-333 or miR-856). An artificial precursor microRNA (pre-amiRNA) is normally processed such that one single stable small RNA is preferentially generated. In some embodiments, viral vectors and particles disclosed herein (e.g., scAAV vectors and scAAVs described herein) comprise a nucleic acid encoding an amiRNA. In some embodiments, the pri-miRNA scaffold of the AmiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

In some embodiments, transgenes may be engineered to express a protein of interest, e.g., a therapeutic protein, and one or more binding sites for an inhibitory nucleic acid (e.g., shRNA, miRNA, amiRNA, etc.). In some embodiments, a transgene comprises 2, 3, 4, 5, 6, 7, 8, 9, 10, or more miRNA binding sites. Transcripts expressing such proteins may also be engineered to contain one or more inhibitory miRNAs (e.g., an miRNA that is not expressed in a host cell). In this way, the transcript, if expressed in a host cell, may be degraded via the inhibitory nucleic acids (e.g., miRNAs, amiRNAs, etc.) expressed by the transcript in the host cell.

The disclosure is based, in part, on transgenes engineered to express transcripts having miRNA or amiRNA binding sites configured to hybridize to miRNAs or amiRNAs that are not endogenously expressed in a host cell (e.g., orthogonal miRNAs). For example, in some embodiments, a construct engineered to express a transgene in a mammalian cell, such as a human cell, comprises a transgene having one or more binding sites for an inhibitory nucleic acid (e.g., miRNA, amiRNA, etc.) that is only endogenously expressed in plant cells or insect cells. In some embodiments, a construct engineered to express a transgene in an insect cell, such as a Sf9 cell, comprises a transgene having one or more binding sites for an inhibitory nucleic acid (e.g., miRNA, amiRNA, etc.) that is only endogenously expressed in mammalian cells or plant cells.

In some embodiments, a transcript comprises one or more binding sites for an miRNA selected from miR-333 (SEQ ID NO: 1) or miR-856 (SEQ ID NO: 2). In some embodiments, a binding site for miR-333 is represented by the sequence set forth in SEQ ID NO: 3. In some embodiments, a binding site for miR-856 is represented by the sequence set forth in SEQ ID NO: 4.

The positioning of inhibitory nucleic acid (e.g., shRNA, miRNA, amiRNA, etc.) binding sites in a transcript may vary. In some embodiments, one or more binding sites for an inhibitory nucleic acid are positioned in a 5' untranslated region (5'UTR) of a transcript. In some embodiments, one or more binding sites for an inhibitory nucleic acid are positioned in an intron. In some embodiments, one or more binding sites for an inhibitory nucleic acid are positioned between the last codon of a last codon and the polyA tail of the transcript. In some embodiments, one or more binding sites for an inhibitory nucleic acid are positioned in 5'UTR and one or more binding sites for an inhibitory nucleic acid are positioned between the last codon of a last codon and the polyA tail of a transcript.

Viral Vectors

Viral vectors present a powerful tool for the delivery of plasmids and genetic material into cells. Adapting plasmid DNA for use with virus-mediated delivery has provided numerous advantages for research, including the delivery of genetic information in traditionally hard-to-transfect cells, such as neurons. Viruses naturally infect host cells and direct them to reproduce the viral genome. Scientists have taken advantage of this process by providing the virus with alternate genomes (e.g., plasmids encoding a nucleic acid or transgene), which can then be replicated once the virus has infected a host cell. In short, researchers can introduce plasmids into a host cell to generate recombinant virus.

For safety reasons, viral genomes used in research have been modified through the removal of certain genes that are required for viral replication. These genes are usually divided among numerous "accessory plasmids" which must also be present in the cell for a viral particle to be produced. The production of viral particles comprising nucleic acid(s) of interest, along with the viral genome, by a host cell is herein referred to as "packaging". The process for the delivery and packaging of nucleic acids into viral genomes varies depending on the viral genome the nucleic acid is encoded in and will be discussed in greater detail for each viral vector below.

Transgenes expressed from viral genomes for packaging in host cells can be toxic (e.g., cytotoxic or detrimental to the fitness of a host cell, and thus can interfere with viral packaging in the host cell. In some embodiments, a transgene expressed from the first nucleic acid is cytotoxic to host cells. In some embodiments, the transgene expressed forms a second structure with high thermal stabilities.

As used herein, the term "recombinant virus" or "recombinant viral particle" refers to a particle produced in a host cell which encapsulates nucleic acid produced from exogenous DNA inserted into the host cell genome is, has been introduced.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells. The skilled artisan will appreciate that in methods described by the disclosure, a host cell may be transfected with 2, 3, 4, 5, 6, 7, 8, 9, 10, or more isolated nucleic acids.

Lentiviral Vectors

Lentiviral vectors are derived from human immunodeficiency virus-1 (HIV-1). The lentiviral genome consists of single-stranded RNA that is reverse-transcribed into DNA and then integrated into the host cell genome. Lentiviruses can infect both dividing and non-dividing cells, making them attractive tools for gene therapy.

The lentiviral genome is around 9 kb in length and contains three major structural genes: gag, pol, and env. The gag gene is translated into three viral core proteins: matrix (MA) proteins, which are necessary for virion assembly and infection of non-dividing cells; capsid (CA) proteins, which form the hydrophobic core of the virion; and nucleocapsid (NC) proteins, which protect the viral genome by coating and associating tightly with the RNA. The pol gene encodes for the viral protease, reverse transcriptase, and integrase enzymes which are essential for viral replication. The env gene encodes for the viral surface glycoproteins, which are essential for virus entry into the host cell by enabling binding to cellular receptors and fusion with cellular membranes. In some embodiments, the viral glycoprotein is derived from vesicular stomatitis virus (VSV-G). The viral genome also contains regulatory genes, including tat and rev. Tat encodes transactivators critical for activating viral transcription, while rev encodes a protein that regulates the splicing and export of viral transcripts. Tat and rev are the first proteins synthesized following viral integration and are required to accelerate production of viral mRNAs.

To improve the safety of lentivirus, the components necessary for viral production are split across multiple vectors. Methods of the current disclosure describe a recombinant lentiviral transfer vector encoding one or more transgenes of interest flanked by long terminal repeat (LTR) sequences. These LTRs are identical nucleotide sequences that are repeated hundreds or thousands of times and facilitate the integration of the transfer plasmid sequences into the host cell genome. Methods of the current disclosure also describe one or more accessory plasmids. These accessory plasmids may include one or more lentiviral packaging plasmids, which encode the pol and rev genes that are necessary for the replication, splicing, and export of viral particles. The accessory plasmids may also include a lentiviral envelope plasmid, which encodes the genes necessary for producing the viral glycoproteins which will allow the viral particle to fuse with the host cell.

Adeno-Associated Virus

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more proteins and/or one or more binding sites for inhibitory nucleic acids (e.g., shRNA, miRNAs, etc.). The transgene may also comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV3, AAV4, AAV5, AAV6, AAV6.2, AAV7, AAV8, AAVrh8, AAV9, AAVrh10, AAVrh39, AAVrh43, AAV2/2-66, AAV2/2-84, AAV2/2-125, and variants thereof. In some embodiments, the isolated nucleic acid comprises a region (e.g., a first region) encoding an AAV2 ITR.

In some embodiments, the isolated nucleic acid further comprises one or more AAV ITRs. In some embodiments, an AAV ITR has a serotype selected from AAV1, AAV2, AAV3, AAV4, AAV5, AAV6, AAV6.2, AAV7, AAV8, AAVrh8, AAV9, AAVrh10, AAVrh39, AAVrh43, AAV2/2-66, AAV2/2-84, AAV2/2-125, and variants thereof. In some embodiments, an AAV ITR is a mutant ITR (mTR) that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) Molecular Therapy 16(10): 1648-1656.

As used herein, the term "self-complementary AAV vector" (scAAV) refers to a vector containing a double-stranded vector genome generated by the absence of a terminal resolution site (TR) from one of the ITRs of the AAV. The absence of a TR prevents the initiation of replication at the vector terminus where the TR is not present. In general, scAAV vectors generate single-stranded, inverted repeat genomes, with a wild-type (wt) AAV TR at each end and a mutated TR (mTR) in the middle. In some embodiments, isolated nucleic acids comprise DNA sequences encoding RNA hairpin structures (e.g. shRNA, miRNA, and amiRNA) that can serve a function similar to a mutant inverted terminal repeat (mTR) during viral genome replication, generating self-complementary AAV vector (scAAV) genomes. For example, in some embodiments, the disclosure provides rAAV (e.g. self-complementary AAV; scAAV) vectors comprising a single-stranded self-complementary nucleic acid with inverted terminal repeats (ITRs) at each of two ends and a central portion comprising a promoter operably linked with a sequence encoding a hairpin-forming RNA (e.g., shRNA, miRNA, amiRNA, etc.). In some embodiments, the sequence encoding a hairpin-forming RNA (e.g., shRNA, miRNA, ami-RNA, etc.) is substituted at a position of the self-complementary nucleic acid normally occupied by a mutant ITR.

"Recombinant AAV (rAAV) vectors" are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The instant disclosure provides a vector comprising a single, cis-acting wild-type ITR. In some embodiments, the ITR is a 5' ITR. In some embodiments, the ITR is a 3' ITR Generally, ITR sequences are about 145 bp in length. Preferably, substantially the entire sequences encoding the ITR(s) is used in the molecule, although some degree of minor modification of these sequences is permissible. The ability to modify ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). For example, an ITR may be mutated at its terminal resolution site (TR), which inhibits replication at the vector terminus where the TR has been mutated and results in the formation of a self-complementary AAV. Another example of such a molecule employed in the present disclosure is a "cis-acting" plasmid containing the transgene, in which the selected transgene sequence and associated regulatory elements are flanked by the 5' AAV ITR sequence and a 3' hairpin-forming RNA sequence. AAV ITR sequences may be obtained from any known AAV, including presently identified mammalian AAV types.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g. AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV1, AAV2, AAV3, AAV4, AAV5, AAV6, AAV6.2, AAV7, AAV8, AAVrh8, AAV9, AAVrh10, AAVrh39, AAVrh43, AAV2/2-66, AAV2/2-84, AAV2/2-125. In some embodiments, an AAV capsid protein is of a serotype derived from a non-human primate, for example scAAV.rh8, AAV.rh39, or AAV.rh43 serotype. In some embodiments, an AAV capsid protein is of an AAV9 serotype.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

Adenoviral Vector

The adenovirus genome is a non-enveloped, large (36-kb) double-stranded DNA (dsDNA) molecule comprising multiple, heavily spliced transcripts. Adenoviruses have high packaging capacity (~8 kilobases) and are able to target a broad range of dividing and non-dividing cells. Adenoviruses do not integrate into the host genome and thus only produce transient transgene expression in host cells. At either end of adenoviral genome are inverted terminal repeats (ITRs). Genes encoded by the adenoviral genome are divided into early (E1-E4) and late (L1-L5) transcripts. Most human adenoviral vectors are based on the Ad5 virus type, which uses the Coxsackie-Adenovirus Receptor to enter cells.

Recombinant adenovirus has the E1 and E3 genes deleted from its genome. Deletion of E1 renders the virus replication incompetent; E1 is supplied by adenovirus packaging cell lines, such as HEK293 cells. E3 is involved in evading host cell immunity and is thus not essential for virus production. Deletion of these two components results in a transgene packaging capacity of >8 kilobases.

Methods of the current disclosure describe recombinant adenoviral vectors encoding nucleic acid(s) of interest. Generation of recombinant adenoviral vectors involves both a transfer vector and an adenoviral vector. The transgene to be packaged in adenovirus is initially placed in a transfer vector. Recombinant transfer vectors containing left and right flanking sequences which are complementary to the sequences at the site of insertion in the adenoviral genome facilitate insertion of the transgene into the adenoviral plasmid by homologous recombination (HR). The left and right sequences are used as templates to repair a DNA DSB in HR, thereby facilitating error-free insertion of the transgene into the adenoviral plasmid. Methods of the current disclosure describe the use of one or more accessory plasmids in a host cell. In the retroviral system, the accessory plasmid is a packaging plasmids which encodes all necessary components for viral packaging except the E1 and the E3 genes. An additional accessory plasmid is required to provide the E1 gene to the packaging cells.

Retroviral Vector

Retrovirus (most commonly, γ-retrovirus) is an RNA virus comprised of the viral genome and several structural and enzymatic proteins, including reverse transcriptase and integrase. Once inside a host cell, the retrovirus uses the reverse transcriptase to generate a DNA provirus from the viral genome. The integrase protein then integrates this provirus into the host cell genome for production of viral genomes encoding the nucleic acid(s) of interest. Retrovirus can package relatively high amounts of DNA (up to 8 kilobases), but are unable to infect non-dividing cells and insert randomly into the host cell genome.

The retroviral transfer and packaging vectors are similar to the lentiviral system described above. Retroviral transfer vectors typically encode a nucleic acid of interest flanked by LTRs, which are derived from Moloney Murine Leukemia Virus (MoMLV) or Murine Stem Cell Virus (MSCV) sequences. Methods of the current disclosure describe the use of one or more accessory plasmids. For retroviruses, the accessory plasmids are a packaging plasmid, which encodes the gag and pol genes, and an envelope plasmid which encodes the env gene. As in the lentiviral system, the gag gene is translated into three viral core proteins: matrix (MA) proteins, which are necessary for virion assembly and infection of non-dividing cells; capsid (CA) proteins, which form the hydrophobic core of the virion; and nucleocapsid (NC) proteins, which protect the viral genome by coating and associating tightly with the RNA. The pol gene encodes for the viral protease, reverse transcriptase, and integrase enzymes which are essential for viral replication.

Cell

A "host cell" refers to any cell that harbors, or is capable of harboring, a substance of interest or of packaging the nucleic acid of interest into a viral particle. Often a host cell is a mammalian cell. Examples of host cells include human cells, mouse cells, rat cells, dog cells, cat cells, hamster cells, monkey cells, insect cells, plant cells, or bacterial cells. Examples of insect cells include but are not limited to *Spodoptera frugiperda* (e.g., Sf9, Sf21), *Spodoptera exigua*, *Heliothis virescens*, *Helicoverpa zea*, *Heliothis subflexa*, *Anticarsia gemmatalis*, *Trichopulsia ni* (e.g., High-Five cells), *Drosophila melanogaster* (e.g., S2, S3), *Antheraea eucalypti*, *Bombyx mori*, *Aedes alpopictus*, *Aedes aegyptii*, and others. Examples of bacterial cells include, but are not limited to *Escherichia coli*, *Corynebacterium glutamicum*, and *Pseudomonas fluorescens*. Examples of yeast cells include but are not limited to *Saccharomyces cerevisiae*, *Saccharomyces pombe*, *Pichia pastoris*, *Bacillus* sp., *Aspergillus* sp., *Trichoderma* sp., and *Myceliophthora thermophila* C1. Examples of plant cells include but are not limited to *Nicotiana* sp., *Arabidopsis thaliana*, *Mays zea*, *Solanum* sp., or *Lemna* sp.

In some embodiments, a host cell is a mammalian cell. Examples of mammalian cells include Henrietta Lacks tumor (HeLa) cells and baby hamster kidney (BHK-21) cells. In some embodiments, a host cell is a human cell, for example a HEK293T cell. A host cell may be used as a recipient of one or more viral transfer vectors and one or more accessory plasmids. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

Aspects of the disclosure relate to compositions and methods for improving vector yield, viral titer, and/or recombinant viral particle (e.g., rAAV particle) production in host cells. In some embodiments, methods described by the disclosure improve vector yield, viral titer, and/or recombinant viral particle (e.g., rAAV particle) by about 2-fold, 3-fold, 4-fold, 5-fold, 6-fold, 7-fold, 8-fold, 9-fold, 10-fold, or more (e.g., 20-fold, 100-fold, 200-fold, 1000-fold, or more) relative to methods of viral particle production that do not employ pairs of orthogonal (with respect to a host cell) inhibitory nucleic acids and cognate binding sites.

EXAMPLES

Example 1

Figure 1:
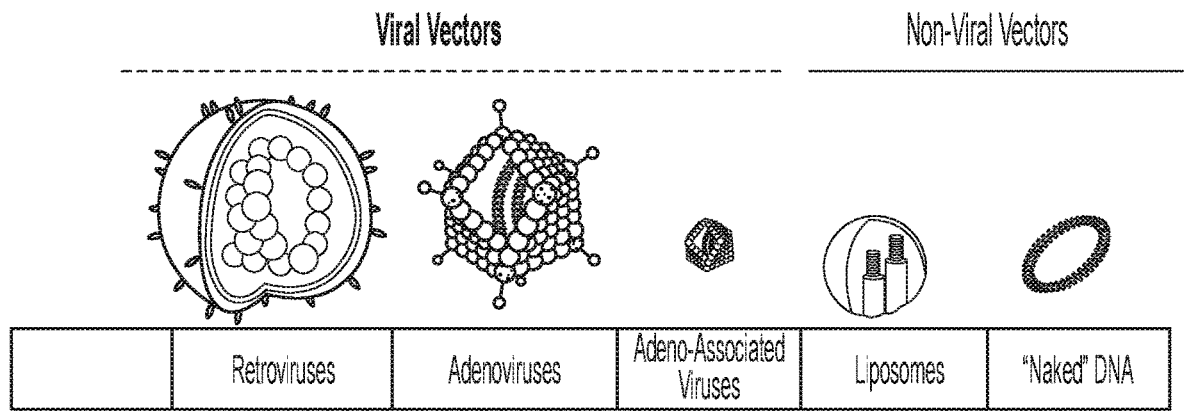
FIG. 1 shows non-limiting examples of viral and non-viral vectors. In some embodiments, vectors shown in FIG.

The disclosure relates, generally, to methods for improving titer and increasing production (e.g., packaging) efficiency of gene expression vectors. FIG. 1 provides several non-limiting examples of gene expression vectors.

Production of viral vectors comprising certain transgenes (e.g., transgene products that are toxic to packaging cells or incompatible with viral vector packaging systems) faces several challenges, for example, very low titer or no production of viral vectors. Possible causes of low titer, or no production of viral vectors, include, for example, bad quality of vector constructs, mutations or deletions of packaging signal/replication origin in vector constructs, secondary structure with high thermal stabilities that hinder vector genome replication, or other factors (e.g., cytotoxic transgenes, or transgenes that interfere with vector genome replication or packaging).

For example, it has been observed that palindrome sequences compromise rAAV genome homogeneity and yield (FIGS. 2A-2C). FIG. 2A shows a schematic of self-complementary AAV (scAAV) plasmids comprising shRNA cassettes targeting Apob, driven by the H1 promoter, or targeting the Firefly luciferase gene (Fluc), driven by the U6 promoter. Briefly, the cells were transformed with the expression constructs and agarose gel analysis was performed. Truncated viral genomes were observed in lanes for all shRNA cassettes but not in control cassette (no shRNA) (FIG. 2B). Vectors were packaged into AAV9 capsids and assessed for yield by qPCR using an EGFP primer/probe set. Data indicate a lower AAV yield when shRNA encoding sequences are in close proximity to the wild-type ITR (wtTR) of the construct (FIG. 2C). Thus, in some embodiments, the secondary structure of a transgene compromises packaging or yield of viral vectors, such as lentiviral vectors.

A schematic depiction of production of 3$^{rd}$ generation lentiviral vectors is provided in FIG. 3. Briefly, packaging cells (e.g., HEK293T) are transformed with four plasmids: a packaging plasmid comprising the gag gene, an Env-encoding plasmid, a Rev-encoding plasmid, and a vector plasmid comprising a transgene.

Transgene cytotoxicity may result in reduced viral replication and/or packaging efficiency, for example in the context of lentiviral vectors. Therefore, production of two lentiviral vectors carrying cytotoxic transgenes (e.g., EGFP-(GR)$_{80}$ (ALS/FTD-related dipeptide repeat protein) or Apol1 (apolipoprotein L1)) was investigated. Cells were infected with a lentiviral vector expressing either GFP (Lenti-GFP, top) or GFP fused to an 80-mer Glycine-Arginine (Lenti-GFP-GR$_{80}$) di-amino acid repeat peptide. Fluorescence imaging shows lower transduction of cells by Lenti-GFP-GR$_{80}$ compared to Lenti-GFP, indicating lower replication or packaging efficiency of the vector comprising cytotoxic protein (GR$_{80}$) relative to vector comprising GFP (FIG. 4).

A strategy for increasing replication and/or packaging of a viral vector comprising an un-packagable (e.g., cytotoxic) transgene was developed (FIG. 5). Briefly, packaging cells are co-transfected with the viral vector production plasmid(s) and a plasmid capable of expressing an interfering RNA molecule (e.g., shRNA, dsRNA, etc.) specific for the unpackageable (e.g., cytotoxic) transgene. Transient silencing of transgene expression during packaging (e.g., mediated by RNAi machinery such as Ago2) increases viral vector replication and packaging, leading to an increased yield.

Cells were infected with a lentiviral vector expressing either GFP (Lenti-GFP, FIG. 6 top), Lenti-GFP-GR$_{80}$ (FIG. 6, middle), or Lenti-GFP-GR$_{80}$ that was packaged during transient gene expression silencing by a plasmid expressing Lenti-GFP-GR$_{80}$-specific shRNA (FIG. 6, bottom). Fluorescence imaging shows lower transduction of cells by Lenti-GFP-GR$_{80}$ compared to Lenti-GFP, indicating lower replication or packaging efficiency of the vector comprising cytotoxic protein (GR$_{80}$) relative to vector comprising GFP. However, significantly increased transduction and expression of GFP-GR$_{80}$ was observed in cells transduced with Lenti-GFP-GR$_{80}$+shRNA-GFP, indicating that transient silencing of transgene expression during vector packaging results in high titer and functional viral vectors.

It has been observed that RNAi potency increases when an increasing number of miRNA binding sites is incorporated into a transgene construct. For example, zero, one, or three miR-122 binding sites were incorporated into a nLacZ expression construct. Huh7 cells were transfected with each construct and nLacZ expression was measured. Data indicate decreased transgene (nLacZ) expression in cells transfected with constructs having one or three miR-122 binding sites (FIG. 8). A similar decrease in transgene expression was also observed in mouse livers (FIG. 8).

FIG. 9 shows specific and efficient gene silencing by the interaction between artificial miRNA (amiRNA) and their target sites. Cells were co-transfected with an EGFP construct comprising multiple miRNA binding sites, specific for either 333T or 856T (which are sequences that are not bound by known mammalian miRNAs), and a plasmid expressing either miR-333 or miR-856 amiRNA. Sequences of miR-333 and miR-856, and their respective binding sites are shown below in Table 1.

TABLE 1

| Name | Sequence | SEQ ID NO: |
|---|---|---|
| miR-333 | UCGAGAAGGUAUAUUGCUGUUG ACAGUGAGCGAAGCAGUUCAUC GCACAGGUUAGUGAAGCCACAG AUGUAACCUGUGCGAUGAACUG CUGUGCCUACUGCCUCGG | 1 |
| miR-856 | UCGAGAAGGUAUAUUGCUGUUG ACAGUGAGCGAUAAUCCUACCA AUAACUUCAGCUAGUGAAGCCA CAGAUGUAGCUGAAGUUAUUGG UAGGAUUAGUGCCUACUGCCUC GG | 2 |
| miR-333 binding site | CGATCGTCGACATTCCTGAGAT CGATCGTCGACATTCCTGAGAT CGATCGTCGACATTCCTGAGAT | 3 |
| miR-856 binding site | GCTGAAGTTATTGGTAGGATTA TGCTGAAGTTATTGGTAGGATT ATGCTGAAGTTATTGGTAGGAT TAT | 4 |

Data indicate silencing of EGFP-333T expression in cells that were co-transfected with miR-333 amiRNA but not miR-856 amiRNA or a shRNA control plasmid. Data indicate silencing of EGFP-856T expression in cells that were co-transfected with miR-856 amiRNA but not miR-333 amiRNA or a shRNA control plasmid.

Based upon the data described above, a second strategy for increasing replication and/or packaging of a viral vector comprising an un-packagable (e.g., cytotoxic) transgene was also developed (FIG. 7). Briefly, one or more (e.g., 3) artificial miRNA (amiRNA) binding sites are engineered into the plasmid comprising the un-packagable (e.g., cytotoxic) transgene. Packaging cells are co-transfected with the viral vector production plasmid(s) and a plasmid capable of expressing an amiRNA that is specific for the binding sites engineered into the production plasmid. During the packaging phase, the amiRNA bind to the target sites located on the transgene and transiently silence transgene expression, resulting in improved viral titer and packaging efficiency.

A lentiviral vector capable of expressing apolipoprotein L1 (Apol1), which typically cannot be packaged using conventional viral vector production procedures, was produced using the strategy outlined in FIG. 7. Briefly, three miR-856 binding sites (3×856T) were incorporated into a Apol1 lentivirus expression construct. Packaging cells were co-transfected with the Apol1 expression construct and a plasmid expressing amiR-856 (FIG. 10, left). Data show that vector titer increases with an increasing amiR-856 concentration, indicating that increased silencing of transgene (e.g., Apol1) expression during packaging increases efficiency of Lenti-Apol1 vector production (FIG. 10, right). Additionally, data indicate that apolipoprotein L1 expressed by the vector (e.g., Lenti-Apol1) that has been packaged during silencing of transgene expression is functional, as evidenced by death of cells infected with Lenti-Apol1 vector but not control Lenti-GFP vector (FIG. 11).

In summary, the data described in this example demonstrate that co-transfection of transient suppression of transgene expression during the packaging phase of viral vector production successfully generated high titer and functional viral (e.g., lentiviral) vectors, even when such vectors comprise cytotoxic or otherwise unpackageable transgenes.

What is claimed is:

1. A method for controlling recombinant lentivirus production yield, the method comprising:
   (i) introducing into a mammalian cell a lentiviral transfer plasmid comprising a transgene encoding an RNA transcript comprising one or more non-mammalian artificial miRNA (amiRNA) binding sites;
   (ii) introducing into the mammalian cell a nucleic acid capable of expressing a non-mammalian amiRNA that specifically binds to the one or more non-mammalian amiRNA binding sites and inhibits translation of the RNA transcript of the transgene; and
   (iii) replicating the lentiviral transfer plasmid within the host cell.

2. The method of claim 1, wherein translation of the RNA transcript of the transgene interferes with viral vector packaging in the host cell.

3. The method of claim 2, wherein a gene product translated from the RNA transcript is cytotoxic or comprises one or more physiochemical characteristics that are detrimental to the fitness of the host cell.

4. The method of claim 1, wherein the one or more non-mammalian amiRNA binding sites are located (a) between the last codon and the polyA tail of the RNA transcript or (b) in a 5' untranslated region (5'UTR) of the RNA transcript.

5. The method of claim 1, wherein the amiRNA comprises the miR-333 sequence set forth in SEQ ID NO: 1, or the miR-856 sequence set forth in SEQ ID NO: 2.

6. The method of claim 1, wherein the host cell further comprises one or more accessory plasmids.

7. The method of claim 1, wherein the lentiviral transfer plasmid and the nucleic acid are introduced into the host cell simultaneously.

8. The method of claim 1, wherein the lentiviral transfer plasmid and the nucleic acid are introduced into the host cell separately.

9. The method of claim 1, wherein the lentiviral transfer plasmid and the nucleic acid are situated on the same plasmid.

10. The method of claim 1, further comprising:
   (iv) isolating a virus particle comprising the lentiviral transfer plasmid from the host cell.

11. The method of claim 1, wherein the one or more non-mammalian amiRNA binding sites comprise a sequence selected from SEQ ID NOs: 3 and 4.

\* \* \* \* \*

SEQUENCE LISTING

```
<160> NUMBER OF SEQ ID NOS: 4

<210> SEQ ID NO 1
<211> LENGTH: 106
<212> TYPE: RNA
<213> ORGANISM: Artificial Sequence
<220> FEATURE:
<223> OTHER INFORMATION: Synthetic Polynucleotide

<400> SEQUENCE: 1
ucgagaaggu auauugcugu ugacagugag cgaagcaguu caucgcacag guuagugaag      60
ccacagaugu aaccugugcg augaacugcu gugccuacug ccucgg                   106

<210> SEQ ID NO 2
<211> LENGTH: 112
<212> TYPE: RNA
<213> ORGANISM: Artificial Sequence
<220> FEATURE:
<223> OTHER INFORMATION: Synthetic Polynucleotide

<400> SEQUENCE: 2
ucgagaaggu auauugcugu ugacagugag cgauaauccu accaauaacu ucagcuagug      60
aagccacaga uguagcugaa guuauuggua ggauuagugc cuacugccuc gg            112

<210> SEQ ID NO 3
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 3
cgatcgtcga cattcctgag atcgatcgtc gacattcctg agatcgatcg tcgacattcc      60
tgagat                                                                66

<210> SEQ ID NO 4
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 4
gctgaagtta ttggtaggat tatgctgaag ttattggtag gattatgctg aagttattgg      60
taggattat                                                             69
```